(12) United States Patent
Frerichs

(10) Patent No.: US 6,955,749 B2
(45) Date of Patent: Oct. 18, 2005

(54) SENSOR FOR MEASURING AN ION CONCENTRATION OR GAS CONCENTRATION

(75) Inventor: Heinz-Peter Frerichs, St. Peter (DE)

(73) Assignee: Micronas GmbH, Freiburg (DE)

( * ) Notice: Subject to any disclaimer, the term of this patent is extended or adjusted under 35 U.S.C. 154(b) by 331 days.

(21) Appl. No.: 10/121,920

(22) Filed: Apr. 12, 2002

(65) Prior Publication Data

US 2002/0170824 A1 Nov. 21, 2002

(30) Foreign Application Priority Data

Apr. 12, 2001 (DE) .......................... 101 18 366

(51) Int. Cl.[7] .......................... G01N 27/26; H01L 23/58
(52) U.S. Cl. .................... 204/416; 204/415; 204/406; 257/253
(58) Field of Search .................... 204/401, 406, 204/416–426, 431; 257/253; 205/789

(56) References Cited

U.S. PATENT DOCUMENTS

| | | | |
|---|---|---|---|
| 4,385,274 A | | 5/1983 | Shimada et al. ........... 324/71.6 |
| 4,411,741 A | | 10/1983 | Janata ......................... 204/1 T |
| 4,671,852 A | * | 6/1987 | Pyke ............................ 438/49 |
| 4,947,104 A | * | 8/1990 | Pyke ........................... 324/71.5 |
| 5,063,081 A | * | 11/1991 | Cozzette et al. .............. 435/4 |
| 5,212,050 A | * | 5/1993 | Mier et al. .................. 430/320 |
| 5,786,235 A | * | 7/1998 | Eisele et al. .................. 438/53 |
| 5,911,873 A | | 6/1999 | McCarron et al. .......... 205/789 |
| 6,306,594 B1 | * | 10/2001 | Cozzette et al. ............... 435/6 |

FOREIGN PATENT DOCUMENTS

| | | |
|---|---|---|
| DE | 3144459 | 10/1982 |
| DE | 4239319 | 4/1993 |
| DE | 4333875 | 4/1995 |
| DE | 19849932 | 5/2000 |
| EP | 0947829 | 10/1999 |

OTHER PUBLICATIONS

Gergintschew et al., "The capacitively controlled field effect transistor (CCFED) as a new low power gas sensor", Elsevier Science S.A., B 35–36, 1996, 285–289.

* cited by examiner

*Primary Examiner*—Nam Nguyen
*Assistant Examiner*—R Michelle Vestal
(74) *Attorney, Agent, or Firm*—O'Shea, Getz & Kosakowski, P.C.

(57) ABSTRACT

The invention relates to a sensor for measuring ion concentration or gas concentration, with a gas- or ion-sensitive layer (6) that has two sensitive partial areas (20 and 21), two conducting areas (1b and 2b), each coupled capacitively through air gaps (9 and 10) with one of the sensitive partial areas (20 and 21), with the capacitances of the couplings being different, and a comparison circuit (1a, 2a, 3, 4, 5) which has at least one first transistor (T1) connected with the first conductive area and a second transistor (T2) connected with the second conductive area, and at least one output at which a signal can be tapped that depends on the potential of sensitive layer (6).

15 Claims, 3 Drawing Sheets

SENSOR FOR MEASURING AN ION CONCENTRATION OR GAS CONCENTRATION

BACKGROUND OF THE INVENTION

The invention relates to the field of sensors for measuring an ion concentration or gas concentration.

Sensors with field effect transistors (FETs) that have an ion-sensitive layer used as a gate are used to measure ion concentrations, with the potential of the layer depending on the ion concentration of a surrounding fluid or gas. For example, U.S. Pat. No. 5,911,873 shows such an ion-sensitive FET (ISFET). In addition, sensors with FETs are known for measuring gas concentrations, for example from U.S. Pat. No. 4,411,741, which have a gas-sensitive layer used as a gate, whose work function depends on the surrounding gas concentration.

Such sensors are generally produced from a drain and a source in a semiconductor substrate by counterdoping, and an insulating layer is grown or deposited on the substrate between the source and the drain. An ion-sensitive layer can be applied directly to this insulating layer. A gas-sensitive layer called a suspended gate FET (SGFET) can be applied at a certain distance. Alternatively, a gate can be applied to the insulator that is controlled capacitively by a gas-sensitive gate applied at a certain distance. This type of sensor is referred to as a capacitive-controlled FET (CCFET), and is described for example in German patent document DE 43 33 875 C2.

In these sensors the charge change caused by the ions to be detected or the change in work function caused by the gas molecules to be detected, is sensed as a change in the gate source voltage and the change in the drain source current caused thereby. The SGFET and CCFET have the advantage that the transducer formed from the substrate, drain, source, and insulating layer can be made independent of the sensitive layer.

A problem with these sensors is their temperature sensitivity. For example, the change in current caused by a temperature change of about 0.5 Kelvin may be greater than the signal change caused by the gas to be detected. In order to compensate for this temperature dependence, it is known that a second identical FET can be formed with a gate that does not have the gas-sensitive layer of the first gate and serves as a reference FET. One disadvantage of this arrangement is that two different gates must be applied in a small space. Another disadvantage is that the two FETs must be located relatively far apart and as a result can have different temperatures. With two different gates, the temperature pattern of the work function is generally different, so that good temperature compensation cannot take place.

Therefore, there is a need for a sensor for measuring an ion concentration or a gas concentration with reduced temperature dependence.

SUMMARY OF THE INVENTION

Briefly, according to an aspect of the invention, a sensor for measuring an ion concentration or a gas concentration couples two sensitive partial areas of a sensitive layer with different capacitances in a comparison circuit. The comparison circuit can be spatially separate from the sensitive layer. The spatial separation is achieved using process technology and can be formed in a small space and therefore with improved thermal coupling of its components over known measuring circuits. The comparison circuit can have two field effect transistors (e.g., MOSFETs) whose gates are connected with both conducting areas and whose source is common. The different control of the transistors measures the change in potential in the sensitive layer. Temperature variations cause the same changes in the transistor properties and result in negligible changes in the measured values.

Any conducting area coupled capacitively with the sensitive layer is applied with the gate of the related MOSFETs of the comparison circuit as a uniform transparent conductive layer, so that additional contacts are not necessary.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
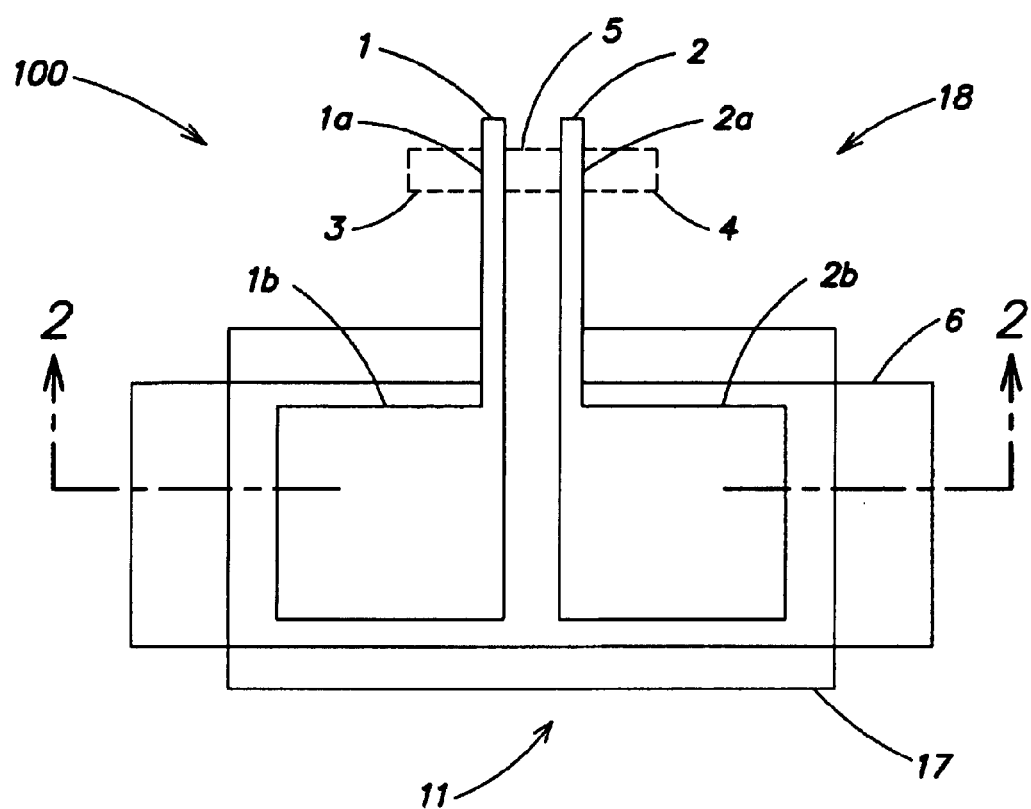
FIG. 1 is a top view of a sensor according to one embodiment of the invention.

FIG. 1 illustrates a sensor 100. The sensor includes a first n-doped drain 3 and a second n-doped drain 4 as well as an n-doped source 5 are formed in a second section 18 of a substrate 11 formed here as a silicon p-substrate by ion implantation. A thin oxide layer is applied between the first and second drains 3, 4 and the source 5, which for example can be about 8–20 nm thick and serve as a gate dielectric. A transducer is formed by the first and second drains 3, 4, the common source 5, and the thin oxide layer.

Figure 2:
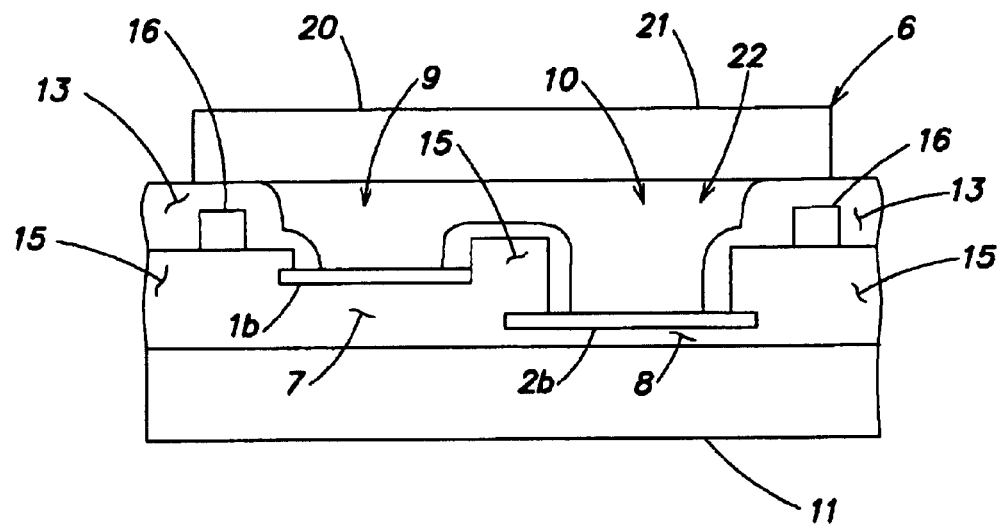
FIG. 2 is a section through the sensor in FIG. 1 along line 2-2.

A thick oxide area with a first thick oxide layer 7 offset in one lengthwise direction with respect to this transducer and a thinner second thick oxide layer 8 that is offset laterally, are formed in a first section 17 of the substrate 11, as shown in FIG. 2. A first conductive layer 1 and a second conductive layer 2 that are offset laterally from one another, are applied to the thin oxide layer and the thick oxide layers 7 and 8, which however are not formed necessarily symmetrically in these embodiments, especially in mirror symmetry to one another.

The conductive layer 1 has a first conductive area 1b applied to the first thick oxide layer 7 and an area that serves as first gate 1a applied to the thin oxide layer between the first drain 3 and the source 5. Correspondingly, the second conductive layer 2 has a the second conductive area 2b applied to second thick oxide layer 8 and an area serving as a second gate 2a applied to the thin oxide layer between the second drain 4 and the source 5. The first and second conductive layers 1, 2 can be applied as poly layers or as metal layers. Two MOSFETs T1 and T2 are formed in the second section 18.

Figure 3:
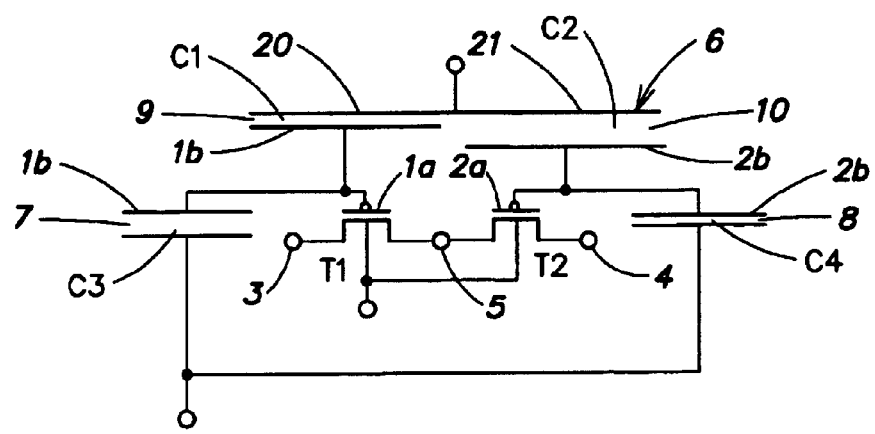
FIG. 3 shows an electrical diagram of the sensor in FIGS. 1 and 2.

A gate 6 with a sensitive layer is applied on additional intermediate layers 13, 15, and 16; the work output of the layer depends on the surrounding gas concentration. An area 22 is formed below the sensitive layer 6, which has a thinner air gap 9 between a first sensitive partial area 20 of the sensitive layer 6 and first conductive area 1b and a thicker second air gap 10 between a second sensitive partial area 21 of the sensitive layer 6 and the second conductive area 2*b*. According to the equivalent diagram in FIG. 3, this air gap acts as capacitors C1 and C2. Accordingly, the conductive areas 1*b* and 2*b* operate with the thick oxide areas 7 and 8 and the substrate as capacitors C3 and C4.

For manufacturing, the first and second conductive layers 1, 2 are first applied to the thick oxide area and the thin oxide layer and structured using a mask process followed by etching. Then intermediate layers 13, 15, and 16 are deposited, structured, and etched over the conductive areas 1*b* and 2*b* so that these are exposed. In addition, the space for the subsequent air gap is formed through which gas exchange can occur beneath the sensitive layer.

Figure 4:
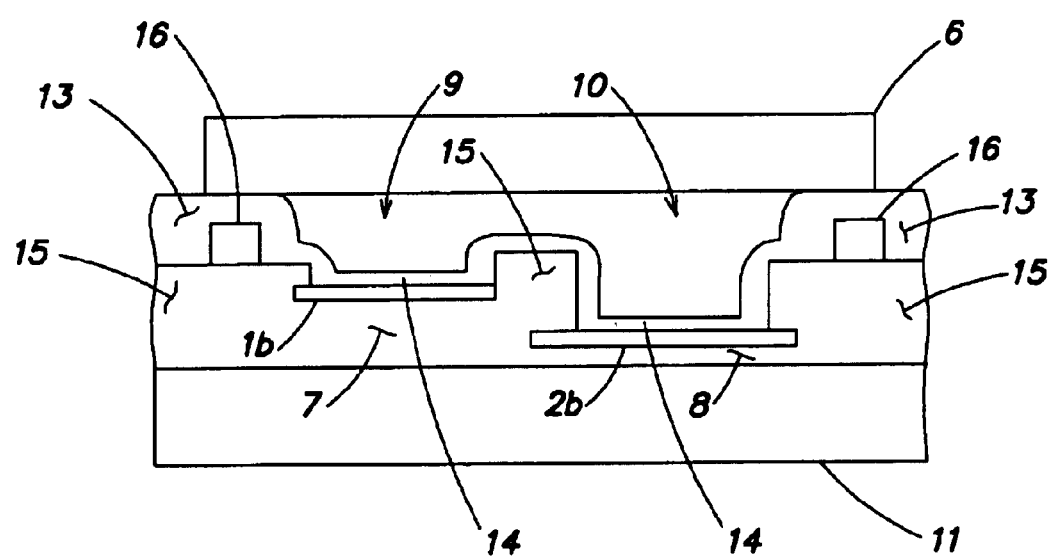
FIG. 4 shows a section according to FIG. 2 through a sensor according to a further embodiment of the invention.

In the embodiment in FIG. 4, an insulating layer 14 is formed on the conductive areas 1*b* and 2*b*, in contrast to the embodiment in FIG. 2. They can be applied together with the intermediate layer 13 and, in contrast to the embodiment in FIG. 2, are not removed by subsequent etching. The sensitive layer 6 can be applied directly to this layer as an ion-sensitive layer. By virtue of such an arrangement, ion concentrations in liquids and gases can be measured.

These embodiments can also be formed with the charge carrier types reversed.

Although the present invention has been shown and described with respect to several preferred embodiments thereof, various changes, omissions and additions to the form and detail thereof, may be made therein, without departing from the spirit and scope of the invention.

What is claimed is:

1. A sensor for measuring an ion concentration or a gas concentration, the sensor comprising a substrate and a sensitive layer, the sensitive layer having a potential that depends on a surrounding gas concentration or ion concentration, the sensitive layer having a first sensitive partial area and a second sensitive partial area, the sensor further comprising a first conductive area capacitively coupled by a first air gap with the first sensitive partial area, a second conductive area capacitively coupled by a second air gap with the second sensitive partial area, wherein the capacitances of the two capacitive couplings are different and wherein the first and second air gaps are of different sizes, the first conductive area capacitively coupled by a first dielectric layer with the substrate and the second conductive area capacitively coupled by a second dielectric layer with the substrate, the sensor further comprising a comparison circuit having a first transistor connected with the first conductive area and a second transistor connected with the second conductive area, the comparison circuit having at least one output signal corresponding to the potential of the sensitive layer.

2. The sensor of claim 1, wherein the first dielectric layer is thicker than the second dielectric layer and the first air gap is smaller than the second air gap.

3. The sensor of claim 2, wherein the two sensitive partial areas are the same size and the two conductive areas are the same size.

4. The sensor of claim 3, wherein the comparison circuit has at least a first and second field effect transistor preferably MOSFETs, on a common substrate, so that a first gate of the first field effect transistor is connected with the first conductive area and a second gate of the second field effect transistor is connected with the second conductive area.

5. The sensor of claim 1, wherein the first and second transistors have a common source area.

6. The sensor of claim 5, wherein the first conductive area and the first gate are made as a first conductive layer, and the second conductive area and the second gate are made as a second conductive layer.

7. The sensor of claim 1, wherein the first and second air gaps are formed as partial areas of a chamber formed beneath the sensitive layer.

8. The sensor of claim 7, wherein the sensitive layer comprises a gas-sensitive layer and conductive areas are open to the first and second air gaps.

9. The sensor of claim 8, wherein the sensitive layer comprises an ion-sensitive layer and is applied to an insulating layer which extends over the first and second conductive areas.

10. The sensor of claim 9, wherein the sensitive gate layer and the conductive areas are formed in a first section of the substrate, and the comparison circuit is formed in a second section of the substrate spaced lengthwise from the first section of the substrate.

11. The sensor of claim 10, wherein the conductive layers are poly layers or metal layers.

12. A sensor for measuring an ion concentration or a gas concentration, the sensor comprising a gate and a substrate spaced apart from each other, the gate comprising a sensitive layer having a work output whose value depends on a surrounding gas concentration or ion concentration, the sensitive layer having first and second sensitive partial areas, the first sensitive partial area being capacitively coupled by a first air gap to a first conductive area, the second sensitive partial area being capacitively coupled by a second air gap to a second conductive area, wherein the first and second air gaps are of different sizes thereby causing the values of the corresponding capacitive couplings to differ, the sensor further comprising a first dielectric layer that capacitively couples the substrate with the first conductive area and a second dielectric layer that capacitively couples the substrate with the second conductive area, the sensor further comprising a comparison circuit having a first transistor connected with the first conductive area and a second transistor connected with the second conductive area.

13. The sensor of claim 12, wherein the first dielectric layer is thicker than the second dielectric layer.

14. The sensor of claim 12, wherein the first air gap is smaller than the second air gap.

15. The sensor of claim 12, wherein the first conductive area is part of a first conductive layer and the second conductive area is part of a second conductive layer.

* * * * *

UNITED STATES PATENT AND TRADEMARK OFFICE
CERTIFICATE OF CORRECTION

PATENT NO. : 6,955,749 B2  Page 1 of 1
DATED : October 18, 2005
INVENTOR(S) : Heinz-Peter Frerichs It is certified that error appears in the above-identified patent and that said Letters Patent is hereby corrected as shown below:

<u>Column 4,</u>
Line 2, after "transistor" insert -- , --.

Signed and Sealed this

Thirteenth Day of December, 2005

JON W. DUDAS
*Director of the United States Patent and Trademark Office*